US005183458A

United States Patent [19]

Marx

[11] Patent Number: 5,183,458

[45] Date of Patent: Feb. 2, 1993

[54] FINGER SUPPORT

[76] Inventor: Ralph H. Marx, 7714 N. 17th Pl., Phoenix, Ariz. 85020

[21] Appl. No.: 827,420

[22] Filed: Jan. 29, 1992

[51] Int. Cl.$^5$ .......... A61F 5/04

[52] U.S. Cl. .......... 602/22; 602/30

[58] Field of Search .......... 602/5, 6, 20, 21, 22, 602/30

[56] References Cited

U.S. PATENT DOCUMENTS

| | | | |
|---|---|---|---|
| 2,237,251 | 4/1941 | Longfellow | 128/37 |
| 2,357,323 | 9/1944 | Goldberg | 128/84 |
| 3,794,019 | 2/1974 | Ritland et al. | 128/77 |

OTHER PUBLICATIONS

Journal A.M.A., Jun. 18, 1938 pp. 2070–2071.

*Primary Examiner*—Robert A. Hafer
*Assistant Examiner*—Brian E. Hanlon
*Attorney, Agent, or Firm*—Warren F. B. Lindsley

[57] ABSTRACT

A support and straightener for finger joint contractures comprising a thin narrow rectangular pliable sheet metal base angularly displaced at one end and having a rigid support aligned with and secured to its bottom surface. The rigid support is angularly displaced from the one end of the base with a threaded aperture extending therethrough. An adjustable screw is threaded through the aperture for engaging with the one end of the base for applying a vernierly adjustable force to the finger joint. A non stretchable strap is mounted around the joint of the finger to be straightened and the support for applying a fixed perpendicular force to the finger at the area effected by the contracture.

3 Claims, 1 Drawing Sheet

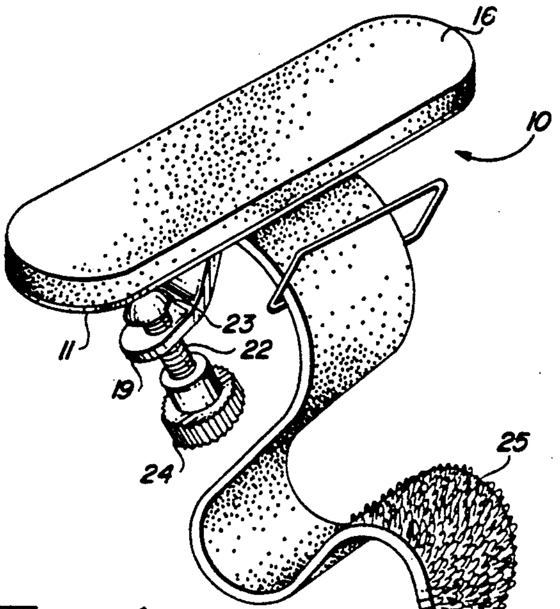
FIG. 1
FIG. 5
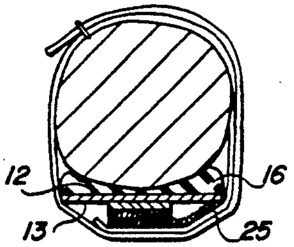
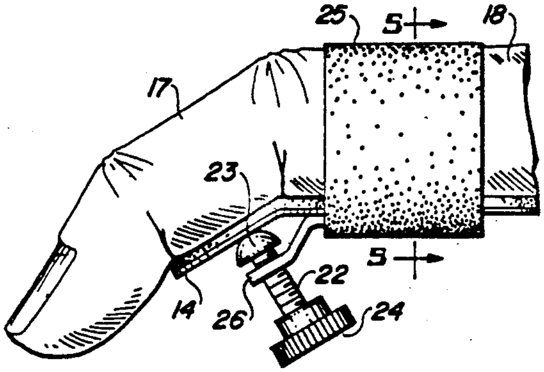
FIG. 4
FIG. 2
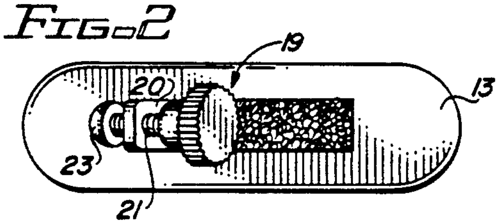
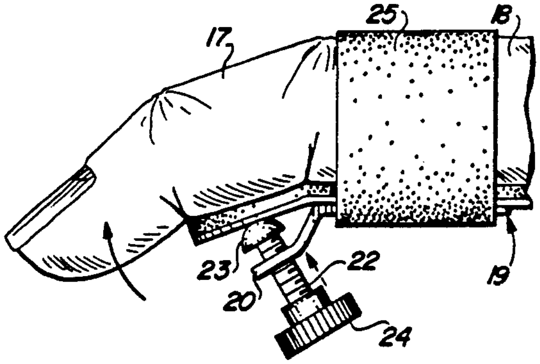
FIG. 6
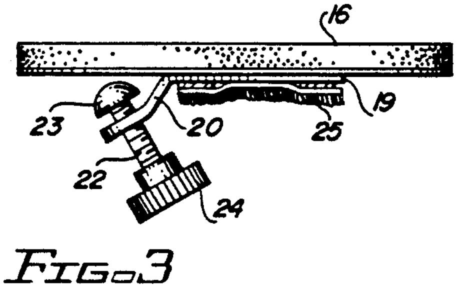
FIG. 3
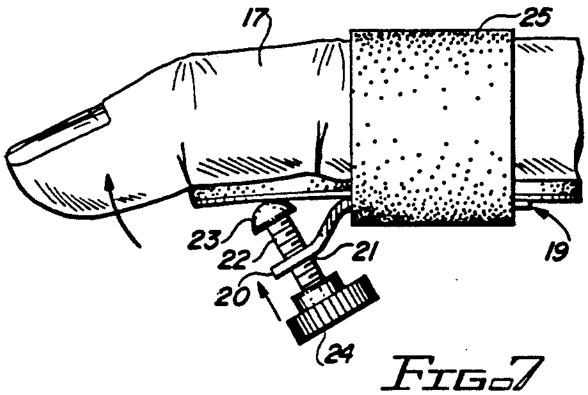
FIG. 7

FINGER SUPPORT

BACKGROUND OF THE INVENTION

This invention relates to surgical supports of the type used to overcome deformities, and more particularly to a finger straightening device for finger joint contractures.

As is well known, finger joints do not always assume a normal position and range of motion after an accident which has caused damage to the tendons of the finger. The tendons and joint capsule structures may be damages or altered causing a contracture of the joint.

Heretofore, the finger supports provided the trade have been bulky and irritating to the skin where attached and some have used wire springs or rubber bands as a force generating means which can not be easily adjusted to the patient's tolerances.

DESCRIPTION OF THE PRIOR ART

U.S. Pat. No. 2,237,251 discloses a finger splint fixation as well as extension to any one of the phalanges without encumbering the metacarpals. The splint comprises a detachable arcuate support for the injured finger while sustaining it in a curved position.

U.S. Pat. No. 2,357,323 discloses an adjustable splint for maintaining a fractured metacarpal bone in anatomical alignment after reduction comprising a rigid frame having a central metacarpal position, a depending phalangeal portion and an angularly extending carpal portion, and an adjustable pressure plate adapted to contact the dorsal surface of the metacarpal region of the patient's hand.

U.S. Pat. No. 3,794,019 discloses a finger support for finger joint contractures and finger straightening comprising a one-piece sheet metal finger support including a base member, an extension member and a strap member applied to the joint to be straightened, and an adjustable screw engageable with the base for applying a vernierly adjustable force to the finger joint.

SUMMARY OF THE INVENTION

In accordance with the invention claimed, a finger contracture support is provided for applying an easily changeable, vermier adjustable and precisely controllable non-elastic force to the joint of a finger to set the joint in a gradually increasing extended position at a rate which the patient can select.

It is, therefore, one object of this invention to provide a new and improved finger support.

Another object of this invention is to provide a finger support which applies a force to the joint with the contracture without causing skin irritation.

A further object of this invention is to provide a relatively inexpensive, expendable, simple to use finger support for joint contractures which can be initially applied and adjusted by a physician as he instructs the patient of its use and simple enough for the patient to use until the contracture is corrected.

Further objects and advantages of the invention will become apparent as the following description proceeds, and the features of novelty which characterize the invention will be pointed out with particularity in the claims annexed to and forming a part of this specification.

BRIEF DESCRIPTION OF THE DRAWING

The present invention may be more readily described with reference to the accompanying drawings in which:

FIG. 1 is a front perspective view of a finger contracture support for use on a finger having a contracture;

FIG. 2 is a bottom view of FIG. 1;

FIG. 3 is a sectional view of FIG. 2;

FIG. 4 is a perspective view of FIG. 1 with a finger in place on the finger support with a VELCRO strap in place;

FIG. 5 is a cross sectional view of FIG. 4 taken along the line 5—5; and FIGS. 6 and 7 show sequential positions of the finger as pressure is being applied to the finger support.

DESCRIPTION OF THE PREFERRED EMBODIMENT

Referring more particularly to the drawing by characters of reference, FIGS. 1–7 disclose a finger contracture support 10 having a generally flat rectangular base support 11 having upper and lower surfaces 12 and 13, respectively. The base support 11 is formed of a malleable metal such as steel or aluminum to allow for bending or cutting to fit the specific requirements of the application while providing the necessary strength while in use. One end of the base portion 11 is provided with a bent or declined portion 14 having a deflection of about 0 to 60 degrees. The top surface 12 of base 11 is provided with a soft padding of any suitable material 16 such as plastic foam which is contoured for covering the entire upper or top surface 12 of base 11 including the declining portion 14. Material 16 serves as a pad to prevent maceration of the skin of the finger and to increase the friction of the skin with the support so that it will not slip.

Referring to FIGS. 1–7 of the drawing, the brace or support 10 is shown as being applied to a finger having a contracture. It can be seen that the tip portion 17 of finger 18 is located on top of padding material 16 on the slanted or inclined portion 14 of the finger support.

Formed as an integral part of the finger support 10 is an angular support 19 which is rivited, soldered or adhesively attached to the bottom or lower surface 13 of base support 11. As noted, the end 20 of the angular support is bent away from base support 11 with its tip bent back on itself to provide an arm having a threaded aperture 21 extending therethrough for receiving a finely threaded adjustment screw 22 the end 23 of which is intended to engage with and selectively displace bent portion 14 in a clockwise direction, as shown, to move the tip of the finger back into a normal position. To aid in threadedly adjusting the adjustment screw 22 its other end is provided with a large knurled head 24 for convenient tightening by hand.

To secure the finger support 10 to the finger of a patient, a non-stretching web or strap 25 is wrapped around the finger and over base support 11 of support 10 and itself to be held there by the known VELCRO type connectors.

From the above, it can be seen that by clockwise rotation of the adjustment screw 22 with its threaded end 23 abutting the lower surface 13 of base support 11, it will apply a finely adjusted non elastic force through the non-stretching straps 25 to the joint of the finger. After the tendons have been stretched by a given adjustment, additional pressure can be carefully and accurately applied at regular intervals via the vermier adjustment screw 22 to set the joint to lengthen the tendons and joint capsule structure in a positive accurate and gradually increasing manner.

An effective adjustable angle proximal interphalangeal joint (PIP) or distal interphalangeal joint (DIP) extension splint is thus provided in accordance with the stated objects of the invention and although but one embodiment of the invention has been illustrated and described, it will be apparent to those skilled in the art that various changes and modifications may be made therein without departing from the spirit of the invention or from the scope of the appended claims.

What is claimed is:

1. A finger support of the type used to overcome deformities comprising:

an elongated rectangular pliable base for supporting a finger having a contracture, one end of said base being bent laterally of its longitudinal axis for receiving the joint of the finger having a contracture, a rigid support mounted to the underside of said base to extend parallel therewith and having one end thereof angularly displaced from said one end of said base, a threaded aperture extending through said one end of said rigid support, an adjustable screw threadedly received in said aperture for extending therethrough and engaging with said one end of said base for applying a vernierly adjustable force through said base to said joint of said finger, and an adjustable non-stretching band mounted around said joint of the finger to be straightened and said support for applying a fixed perpendicular force to said finger at the area effected by the contracture, said adjustable screw engaging said one end of said base at a point spaced from the application of said fixed force of said non-stretching band to said contracture.

2. The finger support set forth in claim 1 wherein: said base is formed of a thin pliable metal.

3. The finger support set forth in claim 1 wherein: said band is formed of a hook and loop material.

* * * * *